US008672869B2

(12) United States Patent
Wratten et al.

(10) Patent No.: US 8,672,869 B2
(45) Date of Patent: Mar. 18, 2014

(54) KIT, SYSTEM AND METHOD OF TREATING MYELOMA PATIENTS

(75) Inventors: Mary Lou Wratten, Medolla (IT); Mauro Atti, Bologna (IT); Antonio Santoro, San Lazzaro di Savena (IT)

(73) Assignee: Bellco S.r.l., Mirandola (MO) (IT)

( * ) Notice: Subject to any disclaimer, the term of this patent is extended or adjusted under 35 U.S.C. 154(b) by 752 days.

(21) Appl. No.: 11/928,881

(22) Filed: Oct. 30, 2007

(65) Prior Publication Data

US 2009/0112146 A1     Apr. 30, 2009

(51) Int. Cl.
*A61M 1/14* (2006.01)
*A61M 1/34* (2006.01)

(52) U.S. Cl.
USPC .......................................... 604/5.04; 604/6.09

(58) Field of Classification Search
USPC ................... 210/645; 604/5.04, 6.09
See application file for complete search history.

(56) References Cited

U.S. PATENT DOCUMENTS

| | | | | |
|---|---|---|---|---|
| 4,350,156 A | * | 9/1982 | Malchesky et al. | 604/6.04 |
| 4,787,974 A | * | 11/1988 | Ambrus et al. | 210/321.8 |
| 5,773,384 A | * | 6/1998 | Davankov et al. | 502/402 |
| 6,497,675 B1 | * | 12/2002 | Davankov | 604/6.09 |
| 7,312,023 B2 | * | 12/2007 | Brady et al. | 435/2 |
| 2005/0029193 A1 | * | 2/2005 | Matson | 210/645 |
| 2005/0115898 A1 | * | 6/2005 | Sternby et al. | 210/636 |
| 2007/0181499 A1 | * | 8/2007 | Roberts et al. | 210/645 |
| 2007/0251882 A1 | * | 11/2007 | Bradwell et al. | 210/646 |

FOREIGN PATENT DOCUMENTS

| | | |
|---|---|---|
| EP | 0787500 B1 | 12/1999 |
| EP | 0958839 B1 | 12/2004 |

OTHER PUBLICATIONS http://www.rohmhaas.com/ionexchange/Pharmaceuticals/Bioprocessing_doc/us_english/CG300.pdf (cannot be attached to Office Action because the Data Sheet file has been encrypted and protected by Rohm and Haas).*
Goldschmidt et al., Multiple myeloma and renal failure, Nephrol Dial Transplant, 15: 301-304, 2000. (not included because document is protected).*
Liu et al., Clinical features of renal insufficiency due to multiple myeloma and related risk factors, The Chinese-German Journal of Clinical Oncology, 4 (1): 47-49, 2005. (not included because the document is protected).*
Cserti et al., Light chain removal by plasmapheresis in myeloma-associated renal failure, Hemapheresis, 47: 511-514, 2007.*
Ying et al., Mapping the binding domain of immunoglobulin light chains for Tamm-Horsfall protein, Am J Pathology, 158 (5): 1859-1866, 2001.*
"Understanding Serum Free Light Chain Assays", International Myeloma Foundation, 2011.*

(Continued)

*Primary Examiner* — Susan Su

(74) *Attorney, Agent, or Firm* — Faegre Baker Daniels LLP

(57) ABSTRACT

Circulating free lambda and kappa free light chains in blood play a role in the pathogenesis of acute renal failure due to myeloma. Coupled plasma filtration and adsorption allows separation of plasma from blood and treatment of the plasma through a cartridge containing a sorbent or resin material, such as hydrophobic divinylbenzene styrenic resins having an average bead diameter of 75 microns, an average pore diameter of 30 nm, and a surface area of 700 m2/g. Lambda and kappa free light chain concentrations progressively decrease during coupled plasma filtration and adsorption treatment resulting in significant reductions by the end of the treatment.

13 Claims, 5 Drawing Sheets

(56) References Cited

OTHER PUBLICATIONS

Pore Size Chart, http://www.spectrumlabs.com/dialysis/poresize.html, printed Jul. 2, 2013.*

EP Application No. 07425010 as filed on Jan. 12, 2007 and entitled Use of Polymeric Resins for the Absorptive Extracorporeal Removal of Inflammatory Mediators in the Treatment of Systemic Inflammation-Related Diseases, 26 pages including receipt and drawings.

Pamphlet, "Understanding Serum Free Light Chain Assays," International Myeloma Foundation, 2006, 13 pages.

Cavo et al., "The Changing Landscape of Myeloma Therapy," The New England Journal of Medicine 354(10): 1076-1078, Mar. 9, 2006.

Bataille et al., "Multiple Myeloma," The New England Journal of Medicine 336(23): 1657-1664, Jun. 5, 1997.

Durie, M.D., Pamphlet, "Concise Review of the Disease and Treatment Option—Multiple Myeloma, Cancer of the Bone Marrow," International Myeloma Foundation, 2006 Edition, 22 pages.

Hutchison et al., "Efficient Removal of Immunoglobulin Free Light Chains by Hemodialysis for Multiple Myeloma: In Vitro and In Vivo Studies," J Am Soc Nephrol 18: 886-895, 2007.

Formica et al., "Coupled Plasma Filtration Adsorption," Contrib Nephrol. Basel, Karger 156: 405-410, 2007.

Ronco et al., "Coupled Plasma Filtration Adsorption: Rationale, Technical Development and Early Clinical Experience," Blood Purif 21: 409-416, 2003.

Ronco et al., "A pilot study of coupled plasma filtration with adsorption in septic shock," Crit Care Med 30(6), 2002, pp. 1250-1255.

European patent application No. 07425010.1, filed Jan. 12, 2007 by Bellco S.p.A., 25 pp.

Merico, et al., "Cytokines involved in the progression of multiple myeloma," Clin Exp Immunol, 1993; 92: 27-31.

Sengul et al., "Myeloma kidney: toward its prevention—with new insights from in vitro and in vivo models of renal injury," JNephrol, 2009; 22: 17-28.

Gado et al., "Role of Interleukin-6 in the Pathogenesis of Multiple Myeloma," Cell Biology International, 2000, vol. 24, No. 4, pp. 195-209.

Hideshima et al., "Molecular Mechanisms of Novel Therapeutic Approaches for Multiple Myeloma," Nature Reviews/Cancer, vol. 2, Dec. 2002, pp. 927-937.

Durie, M.D., "Concise Review of the Disease and Treatment Options—Multiple Myeloma, Cancer of the Bone Marrow," International Myeloma Foundation, 2008/2009 Edition, pp. 1-40.

Edwards et al., "The Pathogenesis of the Bone Disease of Multiple Myeloma," National Health Institutes of Health-Public Access Author Manuscripts, Bone, Jun. 2008; 42(6): 1007-1013.

* cited by examiner

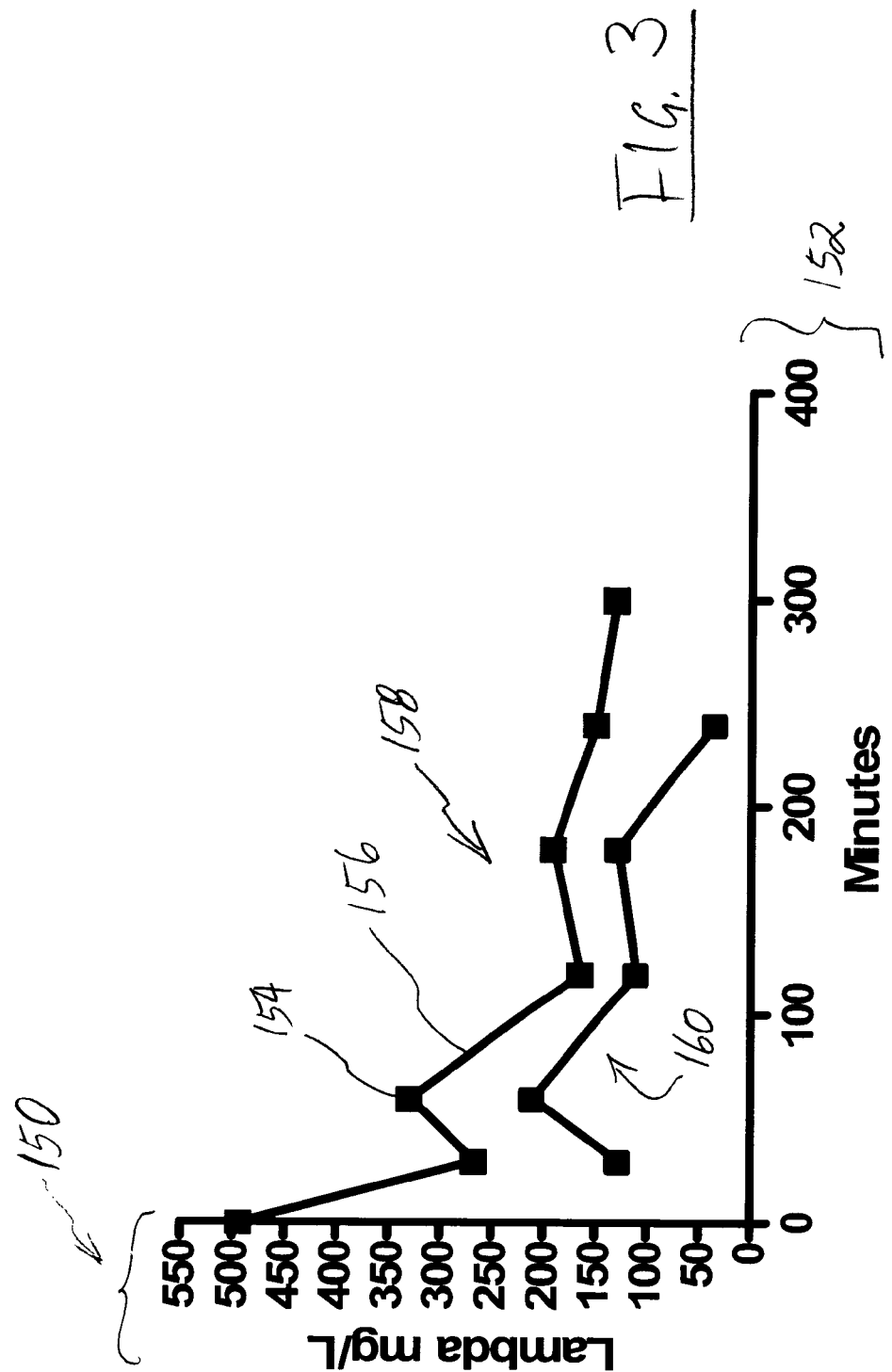

KIT, SYSTEM AND METHOD OF TREATING MYELOMA PATIENTS

TECHNICAL FIELD

The present invention relates to a kit, system and method for reducing either lambda or kappa free light chains or both in the blood of a patient with myeloma. The present invention provides a method, a system and a kit for treating myeloma. The method generally provides for contacting a patient's blood with filters and sorbents or resins, which are effective at lowering the amount of free light chains in the patient's blood. The kit includes filters and sorbents or resins that effectively remove these lambda and/or kappa free light chains from the patient's blood. The system includes the kit and other equipment which can be used to effect the method of the present invention.

BACKGROUND

Myeloma is a cancer of the plasma cells in bone marrow. These plasma cells are known to produce antibodies or immunoglobulins that are used to fight infection and disease in patients. In patients suffering from myeloma, increased replication of particular types of plasma cells can lead to an increased production of monoclonal protein or M-protein. This excess production of M-protein in turn leads to an increase of two types of unbound or free proteins, known as lambda and kappa free light chains, in the patient's blood stream.

Although there are a variety of symptoms associated with myeloma, excess levels of lambda and kappa free light chains have been found to lead to impairment of kidney function in patient's affected with myeloma. For example, in some affected patients, these free light chains have been found to create large accumulations of precipitated free light chains in the kidney. In other affected patients, these free light chains may also be deposited as amyloid in the kidneys as well as other organs.

Known treatments to manage or control the levels of lambda and kappa free light chains in the blood may include the use of specific drugs or removal of the free light chains by plasma exchange or high permeability hemofiltration, hemodialysis or hemodiafiltration, but these treatments are not always satisfactory and can lead to undesired complications such as adverse side effects; drug resistance; inefficient removal of the lambda or kappa free light chains using standard hemofilters for hemodialysis or hemofiltration; loss of albumin and the requirement to use exogenous plasma or substitution fluids with associated risks.

A need exists for new and effective methods of managing or controlling the levels of lambda and kappa free light chains in myeloma patients, including with or without concomitant drug administration during acute periods of this disease.

SUMMARY

An embodiment of a kit for treating patients with myeloma includes a high permeability filter and a cartridge to capture elevated levels of either lambda or kappa free light chains or both; and optionally a dialyzer. The filter includes one or more plasma or ultra filtration materials as are well known in the art, and the cartridge includes one or more sorbent or resin materials as are also well known in the art. The physical parameters of the sorbent or resin material are adjusted to maximize the adsorption of the lambda or kappa free light chains. The dialyzer, if used, further removes residual lambda and kappa free light chains and smaller toxins.

In an embodiment of a method of treating a patient having myeloma, elevated levels of either lambda or kappa free light chains or both are effectively removed from the plasma and/or the ultrafiltrate, which is then re-infused into the patient. An embodiment of the method further includes the step of simultaneously reducing the levels of inflammatory mediators or uremic toxins to prevent or treat acute renal failure.

BRIEF DESCRIPTION OF THE DRAWINGS

FIG. 3 illustrates the effectiveness of a sorbent or resin material in removing lambda free light chains from the plasma.

DETAILED DESCRIPTION

Devices and methods for adsorptive extracorporeal purification of plasma are disclosed in EP 0787500, EP 0958839, and EPO 7425010, all of which are incorporated herein by reference. However, there continues to exist a need for new and effective methods of managing or controlling the levels of lambda and kappa free light chains in myeloma patients.

While multiple embodiments of the instant invention are disclosed, still other embodiments may become apparent to those skilled in the art. The following detailed description shows and describes only illustrative embodiments of the invention, and there is no intent to limit the invention in any form or manner. As such, all alternative embodiments of the invention are within the spirit, scope, and intent of the invention as disclosed herein.

Figure 1:
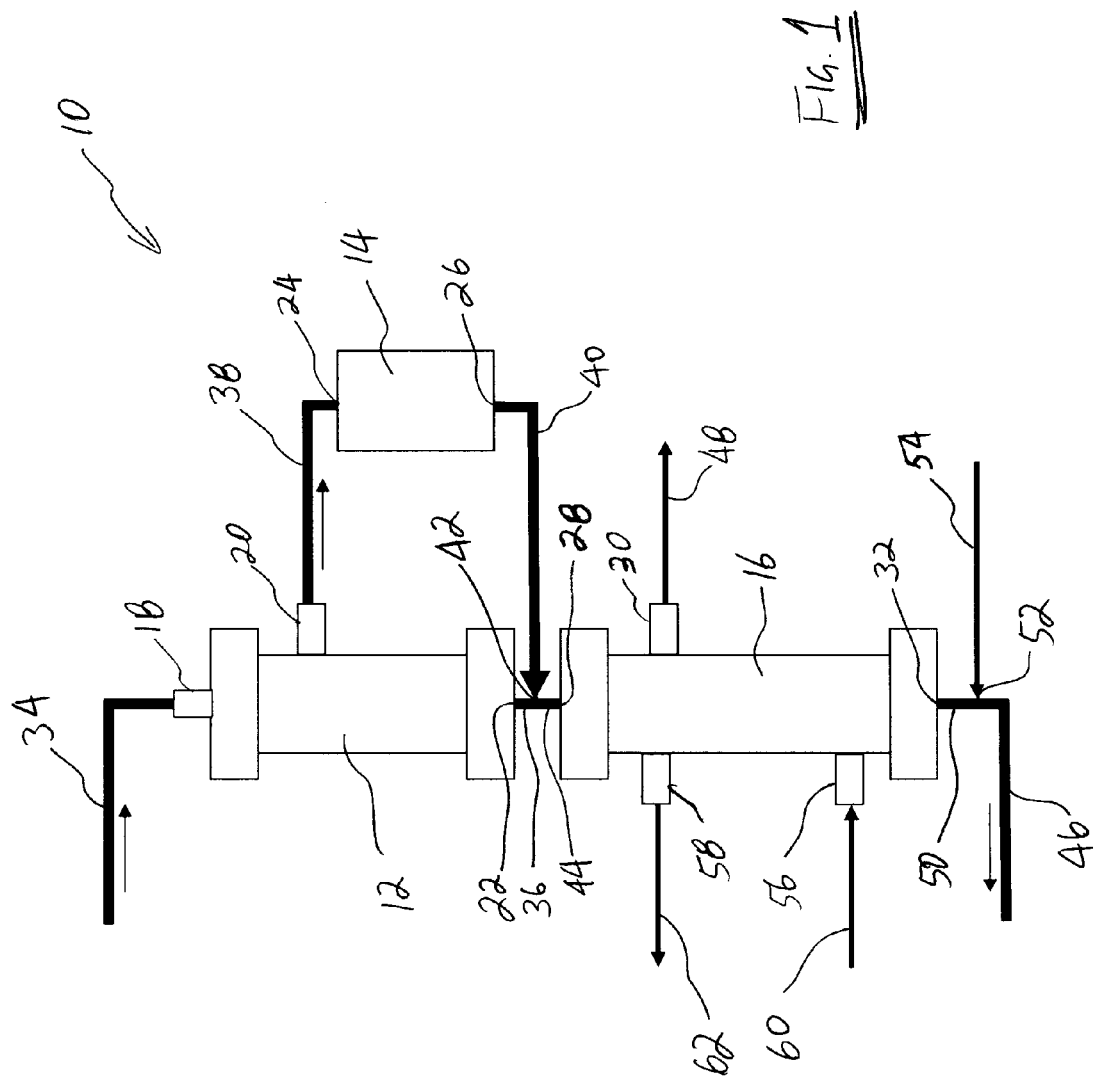
FIG. 1 illustrates an embodiment of a kit including components for treating the blood and plasma of a patient having myeloma.

FIG. 1 illustrates kit 10 for purifying the plasma of a patient having myeloma in accordance with an embodiment of the invention. Kit 10 includes filter 12, sorbent or resin cartridge 14, and dialyzer 16. In an alternate embodiment of kit 10, dialyzer 16 is an optional component and is therefore not included therein. Another embodiment of kit 10 includes a bypass means for directing blood flow around dialyzer 16 and thereby disrupting the flow of blood through dialyzer 16.

In accordance with an embodiment of the invention, filter 12 includes blood inlet port 18, plasma outlet port 20, and blood outlet port 22. In one embodiment the filtration material is a plasma filter. In another embodiment the filtration material is a high permeability filter.

In an embodiment of the invention, sorbent or resin cartridge 14 includes plasma inlet and outlet ports 24 and 26, respectively, and one or more sorbent or resin materials as are well known in the art. In one embodiment the sorbent or resin material is a hydrophobic resin including but not limited to hydrophobic divinylbenzene styrenic resins. In another embodiment the sorbent or resin material is an ion exchange resin. In yet another embodiment the sorbent or resin material is a silica resin. In an alternate embodiment the sorbent or resin material is a combination of two or more of a hydrophobic resin, an ion exchange resin, or a silica resin. In another embodiment the sorbent or resin material is a hydrophobic polystyrene resin. In yet another embodiment the sorbent or resin material is a bonded silica resin. In an alternate embodiment the sorbent or resin material is a combination of two or more of a hydrophobic polystyrene resin, an ion exchange resin, or a bonded silica resin. In another embodiment the adsorption of either lambda or kappa free light chains or both by the sorbent or resin material is maximizable by providing a linear flow velocity for maximum utilization of the adsorption efficacy and capacity of the sorbent or resin material in cartridge 14. In one embodiment the flow velocity of the plasma is varied by changing one or more physical characteristics of the sorbent or resin material, such as the diameter, including bead and pore diameters, cartridge height, volume, and area. In yet another embodiment the sorbent or resin volume is in the range of about 50 ml to about 250 ml.

In accordance with an embodiment of the invention, dialyzer 16 includes blood inlet port 28, ultrafiltrate or dialysate containing ultrafiltrate outlet port 30, blood outlet port 32, dialysis fluid inlet port 56, and dialysate fluid outlet port 58. In one embodiment, dialyzer 16 is a high permeability dialyzer. In another embodiment, dialyzer 16 is a high flux dialyzer. In yet another embodiment, dialyzer 16 is a low flux dialyzer. In an alternate embodiment, dialyzer 16 is a high permeability hemofilter. In another embodiment, dialyzer 16 is a high flux hemofilter. In yet another embodiment, dialyzer 16 is a low flux hemofilter. In one embodiment, dialyzer 16 provides hemodialysis. In another embodiment, dialyzer 16 provides hemodiafiltration. In yet another embodiment, dialyzer 16 provides hemofiltration. In one embodiment, dialyzer 16 provides hemodialysis. In another embodiment, dialyzer 16 provides hemodiafiltration. In yet another embodiment, dialyzer 16 provides hemofiltration. In an alternate embodiment, dialyzer 16 removes small toxins such as those having a molecular weight of less than about 20,000 Daltons.

A method, in accordance with an embodiment of the invention, for treating a patient having myeloma utilizes an embodiment of kit 10 for removing either lambda or kappa free light chains or both from the patient's plasma. The method includes the steps of directing the patient's blood along path 34 into filter 12 through inlet port 18. Plasma in the blood entering filter 12 is extracted therefrom and exits filter 12 through outlet port 20, and the remainder of the blood flows through the filtration material within filter 12. The filtered blood exits filter 12 through outlet port 22 along path 36.

The plasma exiting filter 12 through outlet port 20 flows along path 38 and into sorbent or resin cartridge 14 through inlet port 24. The sorbent or resin material within cartridge 14 extracts, by adsorption, one or more of the lambda and kappa free light chains in the plasma flowing therethrough. The purified plasma exits sorbent or resin cartridge 14 through outlet port 26 along path 40.

The filtered blood exiting filter 12 along path 36, and the purified plasma exiting sorbent or resin cartridge 14 along path 40 are mixed together at junction 42, and the blood mixture flows along path 44. As previously discussed, dialyzer 16 is an optional component for further processing the patient's blood. If dialyzer 16 is not used, then blood flowing along path 44 is further directed along path 46 for re-introduction into the patient.

If dialyzer 16 is used, blood flowing along path 44 enters dialyzer 16 through inlet port 28. Ultrafiltrate, plasmawater, or diffusible toxins in the blood entering dialyzer 16 is extracted therefrom and exits dialyzer 16 through outlet port 30 along path 48. The remainder of the blood flows through dialyzer 16. Dialysis fluid flowing along path 60 enters dialyzer 16 through inlet port 56 and the dialysate fluid exits dialyzer 16 through outlet port 58 along flow path 62. The dialyzed blood exits dialyzer 16 through outlet port 32 along path 50.

At junction 52, if hemofiltration or hemodiafiltration (a net loss of plasma water) has been used, reinfusion fluid along flow path 54 is mixed with the blood exiting dialyzer 16 along path 50. The blood mixture is directed along path 46 for re-introduction into the patient.

Figure 2:
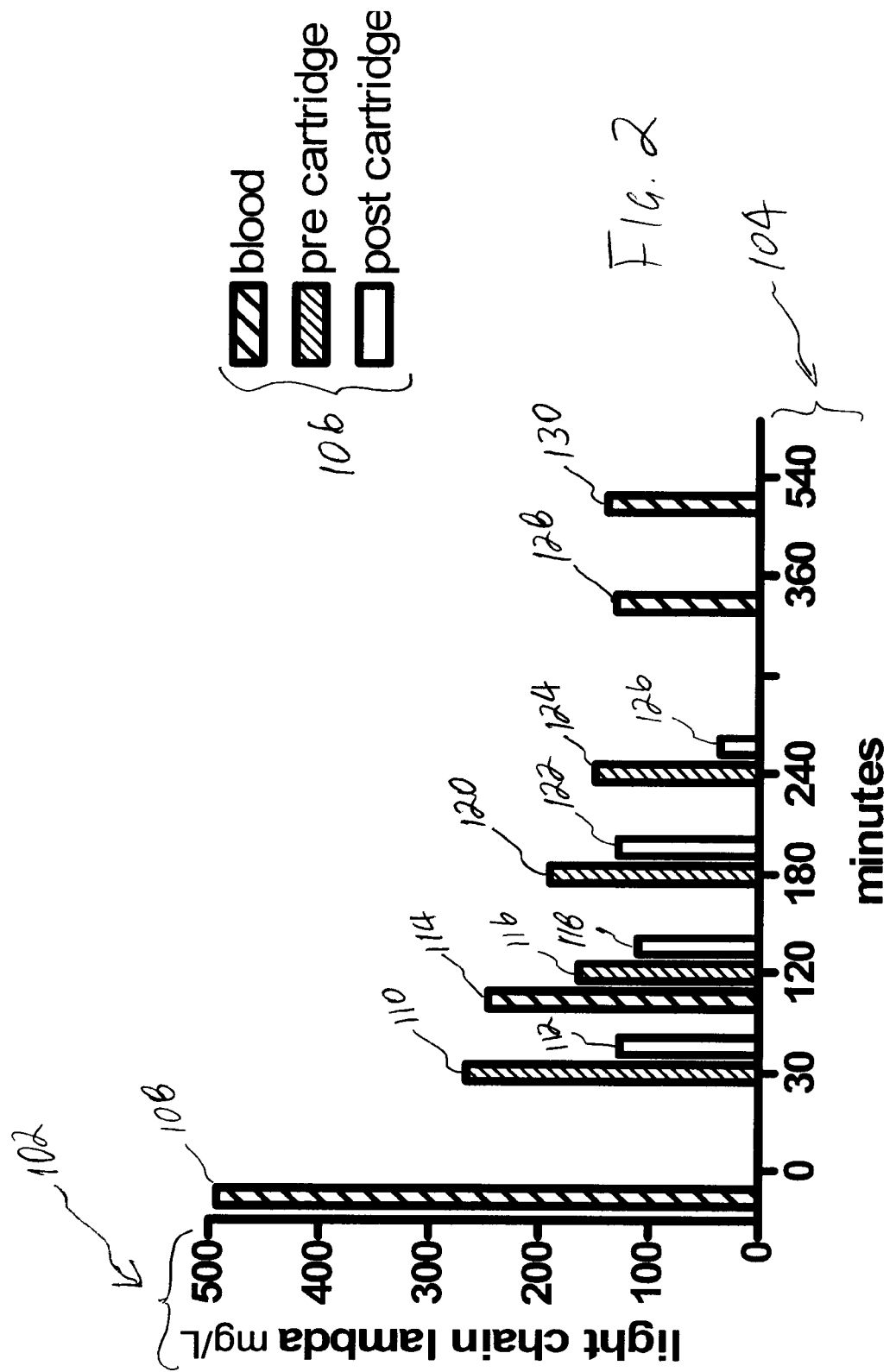
FIG. 2 illustrates the effectiveness of a sorbent or resin material in removing lambda free light chains from the blood.

FIG. 2 illustrates the effectiveness of a sorbent or resin material in removing lambda free light chains from the patient's blood. The illustration of FIG. 2 is in the form of a bar graph having lambda free light chains, in units of mg/L, along its vertical axis 102, and time, in units of minutes, along its horizontal axis 104. Legend 106 is for identifying the vertical rectangles, or bars, extending from horizontal axis 104 such that the height of each vertical bar is indicative of the measured value of the lambda free light chains in mg/L. Vertical bar 108 indicates that just prior to starting the treatment, the patient's blood included about 500 mg/L of lambda free light chains. At about 30 minutes after starting the treatment, the plasma entering and exiting sorbent or resin cartridge 14, respectively, included about 275 mg/L and about 125 mg/L of lambda free light chains as illustrated by vertical bars 110 and 112, respectively. Then, at about 120 minutes after starting the treatment, the patient's blood, and the plasma entering and exiting sorbent or resin cartridge 14, respectively, included about 250 mg/L, about 175 mg/L and about 100 mg/L of lambda free light chains as illustrated by vertical bars 114, 116 and 118, respectively. Next, at about 180 minutes after starting the treatment, the plasma entering and exiting sorbent or resin cartridge 14, respectively, included about 200 mg/L and about 125 mg/L of lambda free light chains as illustrated by vertical bars 120 and 122, respectively. At about 240 minutes after starting the treatment, the plasma entering and exiting sorbent or resin cartridge 14, respectively, included about 150 mg/L and about 25 mg/L of lambda free light chains as illustrated by vertical bars 124 and 126, respectively. As illustrated in FIG. 2, the patient's blood included about 125 mg/L of lambda free light chains at both of about 360 minutes and about 540 minutes after starting the treatment, as respectively indicated by vertical bars 128 and 130.

FIG. 3 illustrates the change in the lambda free light chains in the patient's plasma as it enters and exits sorbent or resin cartridge 14 as the treatment progresses over time. The illustration is in the form of a line graph having lambda free light chains, in units of mg/L, along its vertical axis 150, and time, in units of minutes, along its horizontal axis 152. Solid dark squares, such as that identified by numeral 154, represent measured values of lambda free light chains, in mg/L, at different times after starting the treatment. A straight line, such as line 156, is used for connecting two adjacent measurement values taken at different times and therefore may not represent the actual lambda free light chains at a time between two consecutive measurements. As such, line 158 connects the measured lambda free light chains, in mg/L, entering sorbent or resin cartridge 14 as a function of time after starting the treatment. Likewise, line 160 connects the measured lambda free light chains, in mg/L, exiting sorbent or resin cartridge 14 as a function of time after starting the treatment. As illustrated in FIG. 3, at about 180 minutes after starting the treatment, the plasma entering and exiting sorbent or resin cartridge 14, respectively, includes about 200 mg/L and about 125 mg/L of lambda free light chains.

Figure 4:
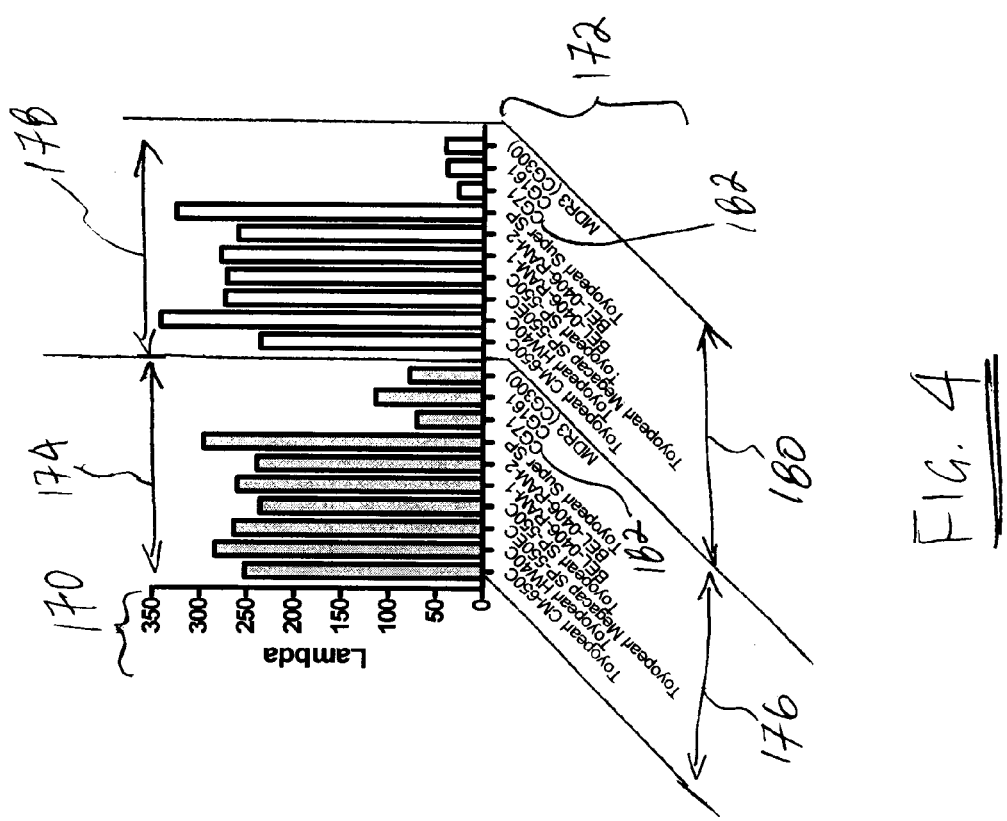
FIG. 4 illustrates the efficacy of in vitro pure resin screens for removing lambda free light chains.

FIG. 4 illustrates measured levels of lambda free light chains, in mg/L, at 30 and 120 minutes after in vitro incubation of the patient's plasma using screens of several different pure resins. The illustration of FIG. 4 is in the form of a bar graph having lambda free light chains, in units of mg/L, along its vertical axis 170, and the pure resins used along its horizontal axis 172. The height of each vertical rectangle, or bar, extending from horizontal axis 172 is indicative of the measured value of the lambda free light chains, in mg/L, in the patient's plasma. Each vertical bar in the group collectively referenced by numeral 174 corresponds with one of the pure resins in the group collectively referenced by numeral 176, and as such is indicative of the lambda free light chains, in mg/L, in the patient's plasma after 30 minutes of in vitro incubation. Likewise, each vertical bar in the group collectively referenced by numeral 178 corresponds to one of the pure resins in the group collectively referenced by numeral 180, and as such is indicative of the lambda free light chains, in mg/L, in the patient's plasma after 120 minutes of in vitro incubation. It should be noted that the pure resins in the groups collectively referenced by numerals 176 and 180 are identical. As such, FIG. 4 indicates that when using pure resin CG71, reference numeral 182, the patient's plasma included about 75 mg/L and about 25 mg/L of lambda free light chains, respectively, after 30 minutes and 120 minutes of in vitro incubation.

FIG. 4 further illustrates that the pure resins CG71, CG161, and MDR3 (CG300) appear substantially more effective at removing lambda free light chains at both 30 minutes and 120 minutes after in vitro incubation relative to using the other pure resins in group 176 (or 180). Physical measurements provided by the manufacturer of the three pure commercially available resins CG71, CG161, and MDR3 (CG300) indicated a bead diameter in the range of about 35 micron to about 75 micron; a pore diameter in the range of about 150 angstrom to about 300 angstrom; and an area in the range of about 500 square-meter/gram to about 900 square-meter/gram. These pure resins are manufactured by Rohm and Haas, Philadelphia, Pa., U.S.A.

Figure 5:
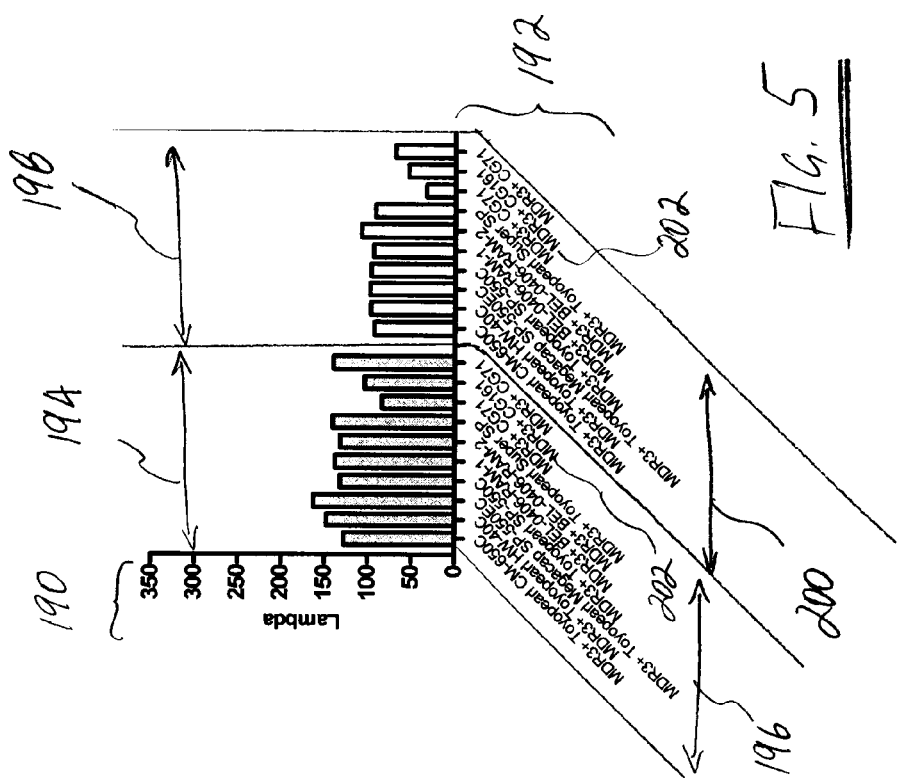
FIG. 5 illustrates the efficacy of in vitro mixed resin screens for removing lambda free light chains.

FIG. 5 illustrates measured levels of lambda free light chains, in mg/L, at 30 and 120 minutes after in vitro incubation using screens of several different mixed resins. The illustration of FIG. 5 is also in the form of a bar graph having lambda free light chains, in units of mg/L, along its vertical axis 190, and the mixed resins used along its horizontal axis 192. The height of each vertical rectangle, or bar, extending from horizontal axis 192 is indicative of the measured value of the lambda free light chains, in mg/L, in the patient's plasma. Each vertical bar in the group collectively referenced by numeral 194 corresponds to one of the mixed resins in the group collectively referenced by numeral 196, and as such is indicative of the lambda free light chains, in mg/L, in the patient's plasma 30 minutes after in vitro incubation. Likewise, each vertical bar in the group collectively referenced by numeral 198 corresponds to one of the mixed resins in the group collectively referenced by numeral 200, and as such is indicative of the lambda free light chains, in mg/L, in the patient's plasma 120 minutes after in vitro incubation. It should be noted that the mixed resins in the groups collectively referenced by numerals 196 and 200 are identical. As such, FIG. 5 indicates that when using mixed resin MDR3+CG161, reference numeral 202, the patient's plasma included about 100 mg/L and about 50 mg/L of lambda free light chains, respectively, after 30 minutes and 120 minutes of in vitro incubation. When compared to the pure resins collectively referenced by numerals 174 and 178 in FIG. 4, the mixed resins collectively referenced by numerals 194 and 198 in FIG. 5 appear to have higher adsorptivity.

Figure 6A:
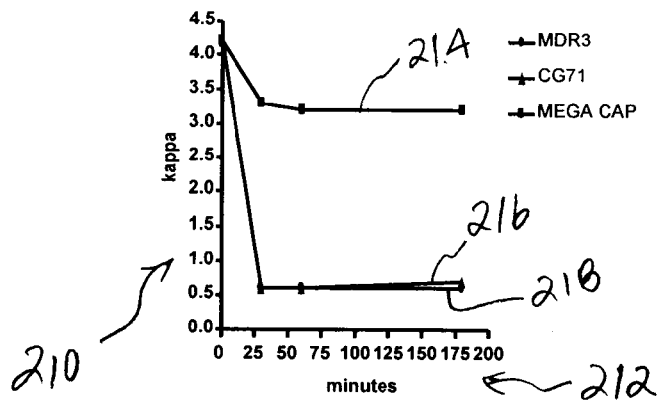
FIG. 6A illustrates the removal rate of kappa free light chains from a first plasma sample by in vitro incubation using different resins.
Figure 6B:
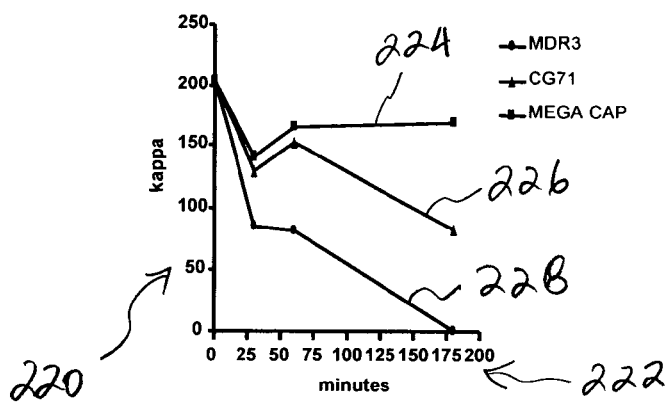
FIG. 6B illustrates the removal rate of kappa free light chains from a second plasma sample by in vitro incubation using different resins.

FIGS. 6A and 6B, respectively, illustrate the change in kappa free light chains over time in a first and a second plasma sample after in vitro incubation using three different pure resins CG71, MDR3, and MEGA CAP. The illustrations are in the form of line graphs having kappa free light chains, in units of mg/L, along respective vertical axes 210 and 220; and time, in units of minutes, along horizontal axes 212 and 222. Solid dark data points in the shape of a circle, a triangle and a square, respectively representing the use of pure resins MDR3, CG71 and MEGA CAP, indicate kappa free light chain measurements after in vitro incubation of each of the first and the second plasma samples. Straight lines are used for connecting two adjacent measurement values taken at different times, and therefore may not represent the actual kappa free light chains at a time between two consecutive measurements. As such, lines 214 and 224 connect the measured kappa free light chains as a function of time after incubation wherein the pure resin MEGA CAP is used when incubating the first and the second plasma samples. Likewise, lines 216 and 226 connect the measured kappa free light chains as a function of time after incubation wherein the pure resin CG71 is used when incubating the first and the second plasma samples. And, lines 218 and 228 connect the measured kappa free light chains as a function of time after incubation wherein the pure resin MDR3 is used when incubating the first and the second plasma samples.

As illustrated in FIG. 6A, the efficacy of pure resins MDR3 and CG71 on kappa free light chains, when used with the first plasma sample, appears to be substantially the same and also appears significantly better than the efficacy of pure resin MEGA CAP on kappa free light chains. Both pure resins MDR3 and CG71 appear to be most effective at about 30 minutes after in vitro incubation.

FIG. 6B illustrates that the efficacy of pure resin MDR3 on kappa free light chains, when used with the second plasma sample, appears to be better than that of pure resin CG71 on kappa free light chains, which in turn appears to have an efficacy better than of pure resin MEGA CAP on kappa free light chains.

Figure 6C:
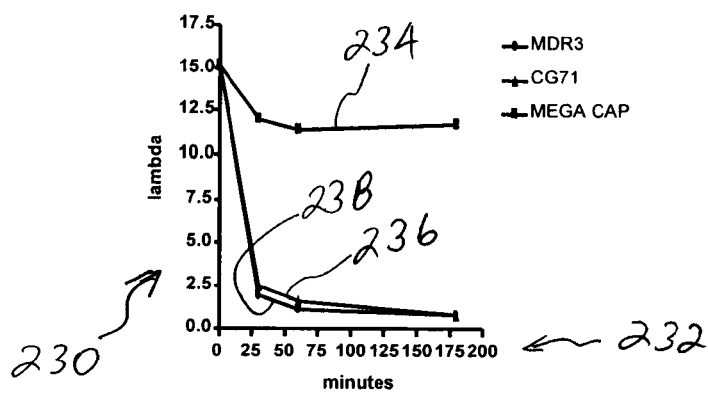
FIG. 6C illustrates the removal rate of lambda free light chains from a third plasma sample by in vitro incubation using different resins.

FIG. 6C illustrates the change in lambda free light chains over time in a third plasma sample after in vitro incubation using three different pure resins CG71, MDR3, and MEGA CAP. The illustration is in the form of line graphs having lambda free light chains, in units of mg/L, along vertical axis 230; and time, in units of minutes, along horizontal axis 232. Solid dark data points in the shape of a circle, a triangle and a square, respectively representing the use of pure resins MDR3, CG71 and MEGA CAP, indicate lambda free light chain measurements after in vitro incubation of the third plasma sample. Straight lines are used for connecting two adjacent measurement values taken at different times, and therefore may not represent the actual lambda free light chains at a time between two consecutive measurements. As such, line 234 connects the measured lambda free light chains as a function of time after incubation wherein the pure resin MEGA CAP is used when incubating the third plasma sample. Likewise, line 236 connects the measured lambda free light chains as a function of time after incubation wherein the pure resin CG71 is used when incubating the third plasma sample. And, line 238 connects the measured lambda free light chains as a function of time after incubation wherein the pure resin MDR3 is used when incubating the third plasma sample.

As illustrated in FIG. 6C, the efficacy of pure resins MDR3 and CG71 on lambda free light chains, when used with the third plasma sample, appears to be substantially the same and also appears significantly better than the efficacy of pure resin MEGA CAP on lambda free light chains. Both pure resins MDR3 and CG71 appear to be most effective at about 30 minutes after in vitro incubation In accordance with an embodiment of the invention, the method described in the foregoing for removing either lambda or kappa free light chains or both from the patient's plasma is also useable for preventing acute renal failure in such patients by removing one or more of uremic toxins and inflammatory mediators such as one or more of interleukin 6 (IL6), vascular endothelial growth factor (VEGF), or tumor necrosis factor.

An alternate embodiment of the invention comprises a system for executing an embodiment of a method for treating myeloma patients, wherein the system includes an embodiment of the kit in combination with other equipment such as, but not limited to, mechanical components, software, hardware, firmware, or some combination thereof.

Various modifications and additions may be made to the exemplary embodiments presented hereinabove without departing from the scope, intent and spirit of the foregoing disclosure. For example, while the disclosed embodiments refer to particular features, the scope of the instant invention is considered to also include embodiments having different combinations of features that do not include all of the features described herein. Accordingly, the scope of the present invention is intended to embrace all such alternatives, modifications, and variations as falling within the scope and intent of the appended claims, including all equivalents thereof.

What is claimed is:

1. A method of treating a patient having myeloma, the method comprising the steps of:
    treating the myeloma patient before development of acute renal failure in the patient by extracting and separating the patient's plasma from the patient's blood;
    removing elevated levels of either lambda or kappa free light chains or both from the patient's plasma by contacting the extracted and separated plasma with a hydrophobic resin, an ion exchange resin, a silica resin or a combination thereof to obtain purified plasma; and
    re-infusing the purified plasma into the patient.

2. The method of claim 1, wherein the step of removing elevated levels of free light chains further comprises removing elevated levels of either lambda or kappa free light chains or both without removing more than about ten percent serum albumin.

3. The method of claim 1, wherein the step of removing elevated levels of free light chains further comprises selectively removing either lambda or kappa free light chains or both by contacting the plasma with a hydrophobic resin.

4. The method of claim 1, wherein the step of removing elevated levels of free light chains further comprises selectively removing either lambda or kappa free light chains or both by contacting the plasma with an ion exchange resin, a bonded silica resin, or a combination thereof.

5. The method of claim 1, wherein the step of removing elevated levels of free light chains further comprises selectively removing either lambda or kappa free light chains or both by contacting the plasma with a hydrophobic polystyrene resin.

6. The method of claim 1, further comprising the step of administering a drug to the patient for treating myeloma or effects thereof.

7. A method of preventing acute renal failure in a patient diagnosed with myeloma, the method comprising the step of purifying the plasma of the myeloma patient before development of acute renal failure in the patient after extracting and separating the patient's plasma from the patient's blood by contacting the extracted and separated plasma with a hydrophobic resin, an ion exchange resin, a silica resin, or a combination thereof to simultaneously reduce levels of either lambda or kappa free light chains or both; and reduce the levels of inflammatory mediators or uremic toxins.

8. The method of claim 7, wherein the inflammatory mediators comprise interleukin 6 in the patient's blood, vascular endothelial growth factor, or tumor necrosis factor or combinations thereof.

9. A method of using a hydrophobic resin, an ion exchange resin, a silica resin or a combination thereof to treat a patient having myeloma, wherein the hydrophobic resin, ion exchange resin, silica resin or combination thereof removes elevated levels of either lambda or kappa free light chains or both from plasma of the patient before development of acute renal failure in the myeloma patient by contacting the patient's plasma with the hydrophobic resin, ion exchange resin, silica resin or combinations thereof after the patient's plasma has been extracted and separated from the patient's blood.

10. The method of claim 9 wherein the lambda or kappa free light chains are removed using a hydrophobic resin.

11. The method of claim 9 wherein the lambda or kappa free light chains are removed using a hydrophobic polystyrene resin.

12. The method of claim 9 wherein the hydrophobic resin, ion exchange resin, silica resin or a combination thereof removes residual lambda and kappa free light chains and smaller toxins with a molecular weight less than 20,000 Daltons.

13. The method of claim 9 wherein the hydrophobic resin, ion exchange resin, silica resin or a combination thereof removes no more than about 10 percent serum albumin.

* * * * *